United States Patent [19]

Snow

[11] Patent Number: 5,041,590

[45] Date of Patent: Aug. 20, 1991

[54] QUATERNARY AMMONIUM FUNCTIONAL SILOXANE SURFACTANTS

[75] Inventor: Steven A. Snow, Midland County, Mich.

[73] Assignee: Dow Corning Corporation, Midland, Mich.

[21] Appl. No.: 460,794

[22] Filed: Jan. 4, 1990

[51] Int. Cl.$^5$ .......................... C07F 7/10; B01F 17/54; B01F 17/18
[52] U.S. Cl. .................................. 556/425; 556/413; 252/357
[58] Field of Search ................. 252/357; 556/413, 425

[56] References Cited

U.S. PATENT DOCUMENTS

| | | | |
|---|---|---|---|
| 3,402,191 | 9/1968 | Morehouse | 252/357 X |
| 3,471,541 | 10/1969 | Morehouse | 252/357 X |
| 3,624,120 | 11/1971 | Yetter | 252/357 X |
| 3,817,739 | 6/1974 | Abbott et al. | 556/413 |
| 3,836,559 | 9/1974 | Morehouse | 252/357 X |
| 4,152,346 | 5/1979 | Seiler et al. | 556/413 |
| 4,918,210 | 4/1990 | Fenton et al. | 252/357 X |
| 4,986,922 | 1/1991 | Snow et al. | 252/357 X |

FOREIGN PATENT DOCUMENTS 1006729 10/1965 United Kingdom .
1549180 7/1979 United Kingdom .

OTHER PUBLICATIONS

Snow et al., "Synthesis and Characterization of Zwitterionic Silicone Sulfobetaine Surfactants", *Langmuir*, vol. 6, No. 2, 1990, pp. 385–391.

*Primary Examiner*—Richard D. Lovering
*Assistant Examiner*—Daniel S. Metzmaier
*Attorney, Agent, or Firm*—Jim L. DeCesare

[57] ABSTRACT

A compound having the formula

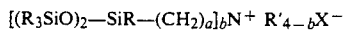

$$[(R_3SiO)_2-SiR-(CH_2)_a]_b N^+ R'_{4-b} X^-$$

wherein R is an alkyl radical having one to six carbon atoms; R' is an alkyl or aryl radical having one to eighteen carbon atoms; X is chloride, bromide, iodide, nitrate, or $RSO_4^-$; a is an integer having a value from one to ten; and b is an integer having a value of two or three. A method of reducing the surface tension of an aqueous solution is also disclosed in which an effective amount of one of the above described compounds is added to the aqueous solution.

9 Claims, No Drawings

QUATERNARY AMMONIUM FUNCTIONAL SILOXANE SURFACTANTS

BACKGROUND OF THE INVENTION

This invention is directed to certain surfactant compositions and to methods of reducing the surface tension of aqueous solutions with the compositions. More particularly, the invention is directed to new quaternary ammonium functional siloxanes.

A surfactant is a compound that reduces surface tension when dissolved in a liquid, decreasing the attractive forces exerted between molecules in the surface region of the liquid, enabling the liquid to spread more readily. Liquids with low surface tensions spread more readily than water, while mercury a higher surface tension liquid spreads less readily than water.

Surfactants exhibit combinations of cleaning, detergency, foaming, wetting, emulsifying, solubilizing, and dispersing properties. They are classified depending upon the charge of the surface active moiety. In anionic surfactants, the moiety carries a negative charge as in soap. In cationic sufactants, the charge is positive. In non-ionic surfactants, there is no charge on the molecule, and in amphoteric surfactants, solubilization is provided by the presence of positive and negative charges in the molecule.

Quaternary ammonium functional siloxanes are not new in the art. For example, in United Kingdom Patent No. 1,549,180, published July 25, 1979, there is described certain fabric conditioning compounds which are dialkylquaternary ammonium terminated linear polydimethylsiloxanes. The compounds of the present invention, in contrast, are monoquaternary ammonium functional polydimethylsiloxanes, and are trialkylsiloxy terminated rather than dialkylquaternary ammonium terminated as the materials in the '180 patent. United Kingdom Patent No. 1,006,729, published Oct. 6, 1965, is directed to certain surfactants which are trialkyl mono(polysiloxy) ammonium chlorides. However, the compounds of the present invention can be distinguished in that the compounds are dialkyl di(polysiloxy) ammonium chlorides, as well as some species which are monoalkyl tri(polysiloxy) ammonium chlorides. Thus, it should be apparent that the present invention is directed toward new and novel compositions of matter not previously known in the prior art.

SUMMARY OF THE INVENTION

This invention relates to a compound having the formula $$[(R_3SiO)_2-SiR-(CH_2)_a]_bN^+R'_{4-b}X^-$$

or $$[(R_3SiO)_2-SiR-(CHR'')_a]_bN^+R'_{4-b}X^-$$

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; a is an integer having a value from one to ten; and b is an integer having a value of two or three.

The invention also is directed to a compound having the formula

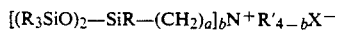

or

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; and a is an integer having a value from one to ten.

A particularly preferred species of the compound comprehended under the foregoing genus is the compound $[(Me_3SiO)_2SiMe(CH_2)_3]_2N^+Me_2I^-$ wherein Me is methyl.

In addition, the invention is directed to an aqueous surfactant composition which is a mixture of at least one liquid and a surfactant compound having the formula set forth above. The surfactant may be present in the mixture in an amount from 0.001 to about five percent by weight.

Further included in this invention is a method of reducing the surface tension of an aqueous solution by adding to the aqueous solution an effective amount of one of the above described compounds.

These and other features, objects, and advantages of the herein described present invention will become more readily apparent when considered in light of the detailed description of the invention which follows.

DETAILED DESCRIPTION OF THE INVENTION

Ammonium compounds in which all of the hydrogen atoms on nitrogen have been substituted by alkyl groups are called quaternary ammonium salts. These compounds may be represented in a general sense by the formula:

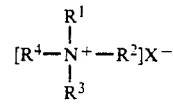

The nitrogen atom includes four covalently bonded substituents that provide a cationic charge. The R groups can be any organic substituent that provides for a carbon and nitrogen bond with similar and dissimilar R groups. The counterion X is typically halogen. Use of quaternary ammonium compounds is based on the hydrophilic portion of the molecule which bears a positive charge. Since most surfaces are negatively charged, solutions of these cationic surface active agents are readily adsorbed to the negatively charged surface.

The compounds of the present invention are of the foregoing type, and can be more particularly illustrated by the formula

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; a is an integer having a value from one to ten; and b is an integer having a value of two or three. These quaternary ammonium functional siloxanes are monoquaternary ammonium functional polydimethylsiloxanes, and are trialkylsiloxy terminated. The compounds of the present invention can also be described as dialkyl di(polysiloxy) ammonium chlorides when the integer a is two, as well as some species which are monoalkyl tri(polysiloxy) ammonium chlorides when the integer a is three. The dialkyl di(polysiloxy) ammonium chloride species is preferred, and especially the particular compound [(Me$_3$SiO)$_2$SiMe(CH$_2$)$_3$]$_2$N$^+$Me$_2$I$^-$ wherein Me is methyl. When employed as a surfactant in accordance with the present invention, the compounds are added in an effective amount which has been found to be from 0.001 to about five percent by weight. Levels of the composition in excess of five percent may also be used, if desired.

As is well known, water has a surface tension of seventy-two dynes per centimeter. It has been found that solutions containing as little as 0.001 percent by weight of the compositions of the present invention possess a surface tension of about sixty dynes per centimeter, and those containing about one percent by weight have a surface tension of the order of about twenty dynes per centimeter. The compositions of the present invention can be used as additives in liquid detergents, cleaners, and automatic dishwashing detergents, and find application as ingredients in powdered detergents for fabric washing machines. These compounds can also be employed as additives in wash cycle softeners and as ingredients in rinse cycle softeners. In addition, the compounds have utility as antistatic agents particularly in wash cycle laundry detergent formulations. The softening effects achieved by the addition of the compounds of the present invention can be enhanced by mixing the compounds with one or more anionic surfactants such as linear alkylbenzene sulfonates, and the compounds may be employed at much lower use levels in comparison to conventional commercial organic based fabric softeners. Reductions as much as fifty to seventy-five percent is not uncommon with the cationic quaternary ammonium functional siloxanes of the present invention.

These novel, cationic, silicone surfactants are prepared with two instead of one siloxane group attached to a quaternary ammonium functional nitrogen atom. This is accomplished by the following series of steps:

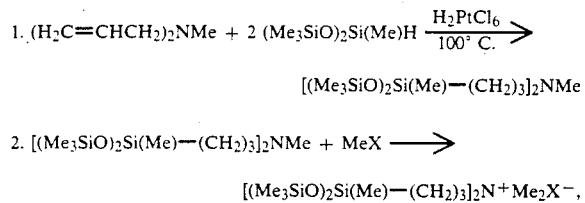

2. [(Me$_3$SiO)$_2$Si(Me)—(CH$_2$)$_3$]$_2$NMe + MeX $\longrightarrow$

[(Me$_3$SiO)$_2$Si(Me)—(CH$_2$)$_3$]$_2$N$^+$Me$_2$X$^-$, where X is Cl, Br, I, or MeSO$_4$.

These compounds are crystalline solids which have varying melting points and solubilities in water. They function as potent surfactants, reducing the surface tension of water from 72 to 21 dyne/cm. They also adsorb very efficiently on negatively charged surfaces such as skin and hair. This adsorption allows for a conditioning or softening effect.

The following example is illustrative of a method for the preparation of the compound [(Me$_3$SiO)$_2$SiMe(CH$_2$)$_3$]$_2$N$^+$Me$_2$I$^-$ wherein Me is methyl.

EXAMPLE

Three hundred grams of the amine [(Me$_3$SiO)$_2$Si(Me)—(CH$_2$)$_3$]$_2$NMe was dissolved in six hundred grams of hexane under nitrogen gas in a two liter flask and heated to reflux. Seventy grams of MeI in fifty grams of hexane was added dropwise to the flask. The product precipitated rapidly. At the conclusion of the dropwise addition, heating of the flask was continued at sixty degrees Centigrade for two hours. The material in the flask was filtered to isolate the crystalline product. One part of the product was mixed with five parts of hexane and the mixture was allowed to sit for about four days in order to leach out any impurities. This mixture was filtered, washed with hexane, and dried under vacuum. The product was characterized by proton nuclear magnetic resonance (NMR) and infrared spectroscopy. The product was identified as the compound [(Me$_3$SiO)$_2$SiMe(CH$_2$)$_3$]$_2$N$^+$Me$_2$I$^-$ wherein Me is methyl.

A series of tests were conducted in order to demonstrate the effectiveness of the silicone surfactant compounds of the present invention in reducing the surface tension of aqueous solutions. Dynamic surface tension data were obtained by a procedure which is a refinement of the standard maximum bubble pressure method, with the aid of a SensaDyne 5000 surface tensiometer manufactured by CHEM-DYNE Research Corporation, Madison, Wis. Dynamic surface tension is a measure of surface activity, and measures the surface energy of the test fluid and the speed of surfactant migration. As noted above, dynamic surface tension is measured utilizing the maximum bubble pressure method with a SensaDyne 5000 surface tensiometer. This instrument measures surface tension by determining the force required to blow bubbles from an orifice and into the test solution. Thus, a low surface energy fluid requires less energy to force a bubble out of the orifice than does a fluid of high surface energy. The speed of surfactant migration, however, is determined by changing the speed of the evolution of the bubbles. With a slow bubble rate, the surfactants have more time to reach the bubble-liquid interface and to orient in order to reduce the surface energy at the interface. With a fast bubble rate, the surfactants have less time to reach the newly formed bubble before the bubble is forced from the orifice. Hence, the surface energy for the fast rate is higher than the surface energy for the slow rate. In the instrument itself, a process gas such as dry nitrogen or clean dry air, is bubbled through two tubes of different diameter that are immersed in the fluid being tested. At each orifice, a bubble is formed in a controlled manner until the bubble reaches a maximum value where it breaks off rising to the surface of the test fluid. Since the two orifices differ in diameter, the two bubbles differ in maximum size and in the maximum pressure required to expand each bubble. This differential pressure is sensed by a transducer and the resulting output signal is used to measure dynamic surface tension directly. The foregoing technique was used in order to determine the dynamic surface tension of an aqueous system, and the results are tabulated in Table I.

Data was also obtained relating to equilibrium surface tension and a DuNouy ring tensiometer was used to generate such data. The DuNouy ring tensiometer was employed in accordance with the method described in ASTM D1331-54-T. Equilibrium surface tension data is shown in Table II.

TABLE I

| Dynamic Surface Tension Measurements for Aqueous Surfactant Solution Containing 0.5% [(Me$_3$SiO)$_2$SiMe(CH$_2$)$_3$]$_2$N$^+$Me$_2$I$^-$ | |
| --- | --- |
| Bubble Rate (H$_2$) | Surface Tension (Dynes/cm) |
| 1 | 20.4 |
| 2 | 21.0 |
| 3 | 21.3 |
| 4 | 21.5 |

TABLE I-continued

Dynamic Surface Tension Measurements for Aqueous Surfactant
Solution Containing 0.5% [(Me$_3$SiO)$_2$SiMe(CH$_2$)$_3$]$_2$N$^+$Me$_2$I$^-$

| Bubble Rate (H$_2$) | Surface Tension (Dynes/cm) |
|---|---|
| 5 | 22.7 |

TABLE II

Equilibrium Surface Tension for Aqueous Surfactant
Solution Containing [(Me$_3$SiO)$_2$SiMe(CH$_2$)$_3$]$_2$N$^+$Me$_2$I$^-$

| Concentration Weight % Surfactant | Surface Tension Dynes/cm |
|---|---|
| 0.001 | 60.5 |
| 0.01 | 52.5 |
| 0.1 | 29.0 |
| 1.0 | 21.5 |

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

What is claimed is:

1. A compound having the formula

[(R$_3$SiO)$_2$—SiR—(CHR")$_a$]$_b$N$^+$R'$_{4-b}$X$^-$ wherein R is an alkyl radical having one to six carbon atoms; R' is an alkyl or aryl radical having one to eighteen carbon atoms; R" is hydrogen or R'; X is chloride, bromide, iodide, nitrate, or RSO$_4^-$; a is an integer having a value from one to ten; and b is an integer having a value of two or three.

2. The compound [(Me$_3$SiO)$_2$SiMe(CH$_2$)$_3$]$_2$N$^+$Me$_2$I$^-$ wherein Me is methyl.

3. A compound having the formula

[(R$_3$SiO)$_2$—SiR—(CHR")$_a$]$_2$N$^+$R'$_2$X$^-$ wherein R is an alkyl radical having one to six carbon atoms; R' is an alkyl or aryl radical having one to eighteen carbon atoms; R" is hydrogen or R'; X is chloride, bromide, iodide, nitrate, or RSO$_4^-$; and a is an integer having a value from one to ten.

4. The method of reducing the surface tension of an aqueous solution comprising adding to the aqueous solution an effective amount of a compound having the formula

[(R$_3$SiO)$_2$—SiR—(CHR")$_a$]$_b$N$^+$R'$_{4-b}$X$^-$ wherein R is an alkyl radical having one to six carbon atoms; R' is an alkyl or aryl radical having one to eighteen carbon atoms; R" is hydrogen or R'; X is chloride, bromide, iodide, nitrate, or RSO$_4^-$; a is an integer having a value from one to ten; and b is an integer having a value of two or three.

5. The method of claim 4 in which the compound is [(Me$_3$SiO)$_2$SiMe(CH$_2$)$_3$]$_2$N$^+$Me$_2$I$^-$ wherein Me is methyl.

6. The method of claim 5 in which the compound is added to the aqueous solution in an amount from 0.001 to about five percent by weight.

7. The method of reducing the surface tension of an aqueous solution comprising adding to the aqueous solution an effective amount of a compound having the formula

[(R$_3$SiO)$_2$—SiR—(CHR")$_a$]$_2$N$^+$R'$_2$X$^-$ wherein R is an alkyl radical having one to six carbon atoms; R' is an alkyl or aryl radical having one to eighteen carbon atoms; R" is hydrogen or R'; X is chloride, bromide, iodide, nitrate, or RSO$_4^-$; and a is an integer having a value from one to ten.

8. The method of claim 7 in which the compound is [(Me$_3$SiO)$_2$SiMe(CH$_2$)$_3$]$_2$N$^+$Me$_2$I$^-$ wherein Me is methyl.

9. The method of claim 7 in which the compound is added to the aqueous solution in an amount from 0.001 to about five percent by weight.

* * * * *